(12) United States Patent
McMillan et al.

(10) Patent No.: US 10,709,340 B2
(45) Date of Patent: Jul. 14, 2020

(54) AUTOMATED FITTED CUFF BLOOD PRESSURE AND ARM CIRCUMFERENCE MEASURING DEVICE

(71) Applicant: HIGI SH LLC, Chicago, IL (US)

(72) Inventors: Bjorn McMillan, Thousand Oaks, CA (US); David Erceg, South Pasadena, CA (US); Jeffrey D. Flammer, Scottsdale, AZ (US); Rene Nunez, Pacoima, CA (US); Colin Kenneth Hill, San Dimas, CA (US); John R. Collins, Claremont, CA (US)

(73) Assignee: HIGI SH LLC, Chicago, IL (US)

( * ) Notice: Subject to any disclaimer, the term of this patent is extended or adjusted under 35 U.S.C. 154(b) by 274 days.

(21) Appl. No.: 15/858,085

(22) Filed: Dec. 29, 2017

(65) Prior Publication Data

US 2018/0184924 A1    Jul. 5, 2018

Related U.S. Application Data

(60) Provisional application No. 62/440,992, filed on Dec. 30, 2016.

(51) Int. Cl.
*A61B 5/022* (2006.01)
*A61B 5/021* (2006.01)
*A61B 5/00* (2006.01)

(52) U.S. Cl.
CPC ...... *A61B 5/02141* (2013.01); *A61B 5/02225* (2013.01); *A61B 5/02233* (2013.01); *A61B 5/6824* (2013.01)

(58) Field of Classification Search
CPC ....... A61B 5/0476–04847; A61B 5/107–1073; A61B 5/022–0235; A61B 5/02141
See application file for complete search history.

(56) References Cited

U.S. PATENT DOCUMENTS

| 3,935,984 A | * | 2/1976 | Lichowsky | A61B 5/022 600/499 |
| 4,109,646 A | * | 8/1978 | Keller | A61B 5/02241 600/499 |

(Continued)

FOREIGN PATENT DOCUMENTS

| EP | 0332395 A2 | 9/1989 |
| EP | 1384549 A2 | 1/2004 |

(Continued)

OTHER PUBLICATIONS

"Omron Unveils Blood Pressure Monitor Modules for OEM Applications." Electronic Specifier. Dec. 3, 2009. https://www.electronicspecifier.com/communications/omron-unveils-blood-pressure-monitor-modules-for-oem-applications (Year: 2009).*

(Continued)

*Primary Examiner* — Meredith Weare
(74) *Attorney, Agent, or Firm* — Zarley Law Firm, P.L.C.

(57) ABSTRACT

A blood pressure device having a cylindrical drum cuff housing adapted to measure the circumference of either a right or left arm and administer a blood pressure test. The drum cuff housing is connected to a knuckle support assembly adapted to provide freedom of movement for postural positioning before and during the blood pressure test.

16 Claims, 5 Drawing Sheets

(56) References Cited

U.S. PATENT DOCUMENTS

| | | | | |
|---|---|---|---|---|
| 4,206,765 | A * | 6/1980 | Huber | A61B 5/02141 |
| | | | | 600/490 |
| 4,274,424 | A * | 6/1981 | Kimura | A61B 5/02233 |
| | | | | 600/499 |
| 4,943,878 | A * | 7/1990 | Lin | G11B 15/26 |
| | | | | 360/132 |
| 5,201,319 | A | 4/1993 | Negishi | |
| 5,595,180 | A | 1/1997 | Ogura et al. | |
| 5,697,376 | A * | 12/1997 | Nomura | A61B 5/0225 |
| | | | | 600/300 |
| 6,336,044 | B1 | 1/2002 | Ghiassi et al. | |
| 7,445,600 | B1 * | 11/2008 | Carr | A61B 5/0059 |
| | | | | 600/300 |
| 8,753,282 | B2 | 6/2014 | Kukita et al. | |
| 2005/0187485 | A1 * | 8/2005 | Fumuro | A61B 5/02233 |
| | | | | 600/499 |
| 2006/0202678 | A1 | 9/2006 | Nayak et al. | |
| 2008/0132795 | A1 * | 6/2008 | Ghigini | A61B 5/02233 |
| | | | | 600/490 |
| 2008/0146950 | A1 * | 6/2008 | Fumuro | A61B 5/022 |
| | | | | 600/499 |
| 2008/0243011 | A1 * | 10/2008 | Hori | A61B 5/0225 |
| | | | | 600/499 |
| 2010/0185104 | A1 * | 7/2010 | Kim | A61B 5/02233 |
| | | | | 600/499 |
| 2011/0009757 | A1 * | 1/2011 | Sano | A61B 5/02233 |
| | | | | 600/499 |
| 2011/0288382 | A1 * | 11/2011 | Finburgh | A61B 5/022 |
| | | | | 600/301 |
| 2014/0350418 | A1 | 11/2014 | Knopfel | |
| 2015/0342474 | A1 * | 12/2015 | Collins | A61B 5/02233 |
| | | | | 600/490 |
| 2016/0324524 | A1 * | 11/2016 | Smith | A61B 17/115 |
| 2019/0290372 | A1 * | 9/2019 | Arnold | A61B 34/32 |

FOREIGN PATENT DOCUMENTS

| | | |
|---|---|---|
| EP | 1932468 A2 | 6/2008 |
| GB | 487545 | 6/1938 |

OTHER PUBLICATIONS

Smith, Liz, New AHA Recommendations for Blood Pressure Measurement, Am Fam Physician, Oct. 1, 2005;72(7): 1391-1398.

ABOV Semiconductor, Blood Pressure Monitor, retrieved on Feb. 21, 2018, retrieved from <https://web.archive.org/web/20160910225026/http://www.abov.co.kr/en/index.php?Depth1=4&Depth2=4&Depth3=1.>; dated Sep. 10, 2016.

International Searching Authority, "Notification of Transmittal of the International Search Report and The Written Opinion of the International Searching Authority", for PCT/US2017/069151, dated Mar. 12, 2018, 12 pages.

* cited by examiner

AUTOMATED FITTED CUFF BLOOD PRESSURE AND ARM CIRCUMFERENCE MEASURING DEVICE

CROSS REFERENCE TO RELATED APPLICATION

This application claims the benefit to Provisional Application U.S. Ser. No. 62/440,992 filed on Dec. 30, 2016.

BACKGROUND OF THE INVENTION

The present invention is directed to a blood pressure (BP) monitoring device, and more particularly to an automated device, that measures the circumference of an arm and administers a blood pressure test using a method that mimics a doctor's manual fitted cuff. It further allows the user to get a more accurate BP result using a system that gives freedom of movement for postural positioning before and during BP measurement.

Automated blood pressure cuffs are known in the art. Recently the FDA has established a new set of ANSI guidelines that make it more difficult for a blood pressure system to pass required accuracy testing to allow a system to be placed on the market.

Fixed circumference automatic cuff designs are limited in usefulness. Some have a cuff design that precludes individuals with both large and small arm circumferences from taking a blood pressure test, or, the accuracy of the test is questionable.

Most designs have a fixed metal or plastic housing that do not allow a wide range of users to achieve the American Heart Association's (AHA) recommendations for postural positioning during a blood pressure test increasing the potential for inaccuracy. They also use a system where the bladder inflates until it pins the arm. This process, due to variability in the volume of air in the bladder and the uncertainty in repeatable pressure points used to constrict the brachial artery, leads to inaccurate and inconsistent results. These systems also fail to support the elbow properly, or at all, for certain individuals as recommended by the AHA. Therefore, there is a need in the art for a device that addresses these deficiencies.

An objective of the present invention is to provide a blood pressure measuring device that is more accurate than fixed circumference automatic cuff designs.

Another objective of the present invention is to provide a blood pressure measuring device that measures the circumference of a user's arm.

A still further objective of the present invention is to provide a blood pressure measuring device that provides freedom of movement for postural positioning.

These and other objectives will be apparent to those of ordinary skill in the art based upon the following written descriptions, drawings, and claims.

SUMMARY OF THE INVENTION

A blood pressure device having a cylindrical drum cuff housing adapted to measure the circumference of an arm and administer a blood pressure test simultaneously or after the arm measurement. The cylindrical drum cuff housing is associated with a direct drive assembly. The direct drive assembly includes a motor inside of a reel with an encoder attached to the motor. A flexible lead band material is connected to and wrapped around the reel and has a sensor associated with the flexible lead band material.

A bladder is attached to an inner surface of the flexible lead band material. The bladder is connected to a pump having a source of pressurized air to inflate the pump. Both the bladder and the flexible lead band material are disposed within a protective skirt.

The cylindrical drum cuff housing is connected to a knuckle support assembly. The knuckle support assembly tilts, slides, and rotates to provide freedom of movement for postural positioning and more accurate measurement.

DETAILED DESCRIPTION OF THE PREFERRED EMBODIMENT

Figure 1:
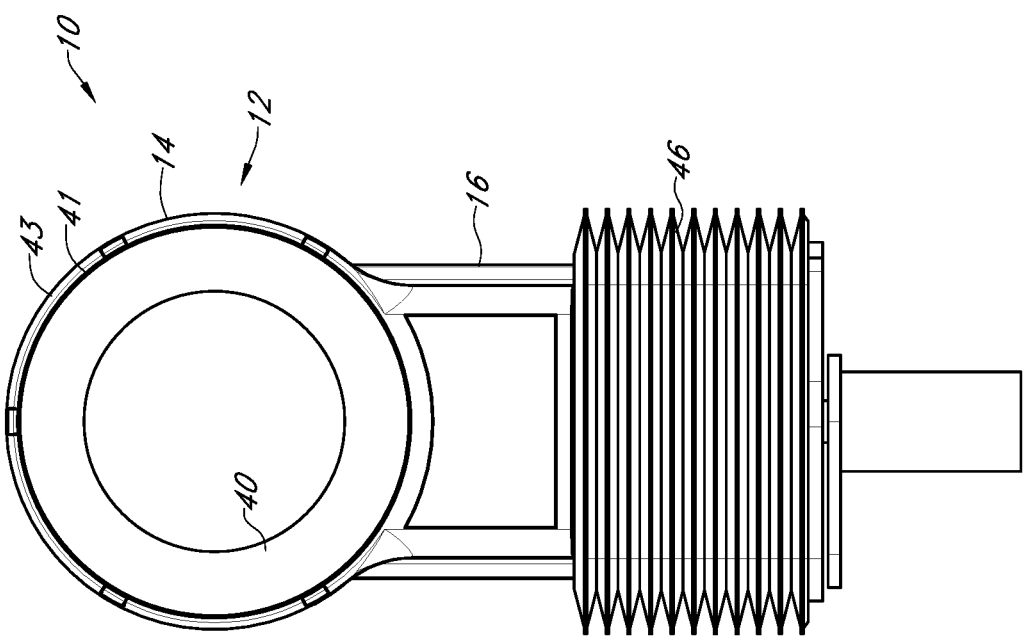
FIG. 1 is an end view of a blood pressure device.
Figure 2:
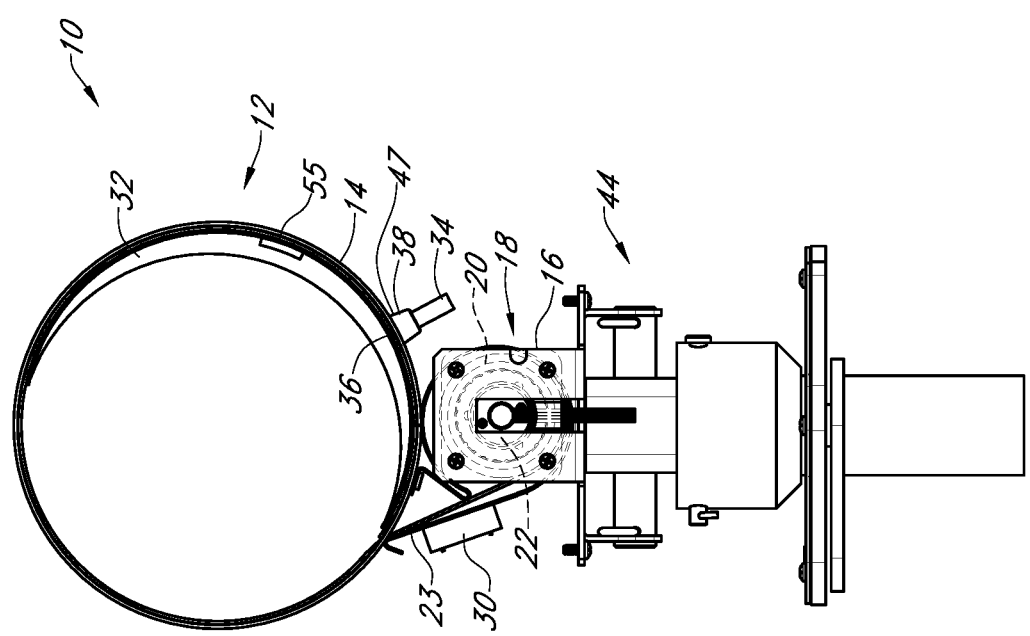
FIG. 2 is a sectional end view of a blood pressure device.
Figure 3:
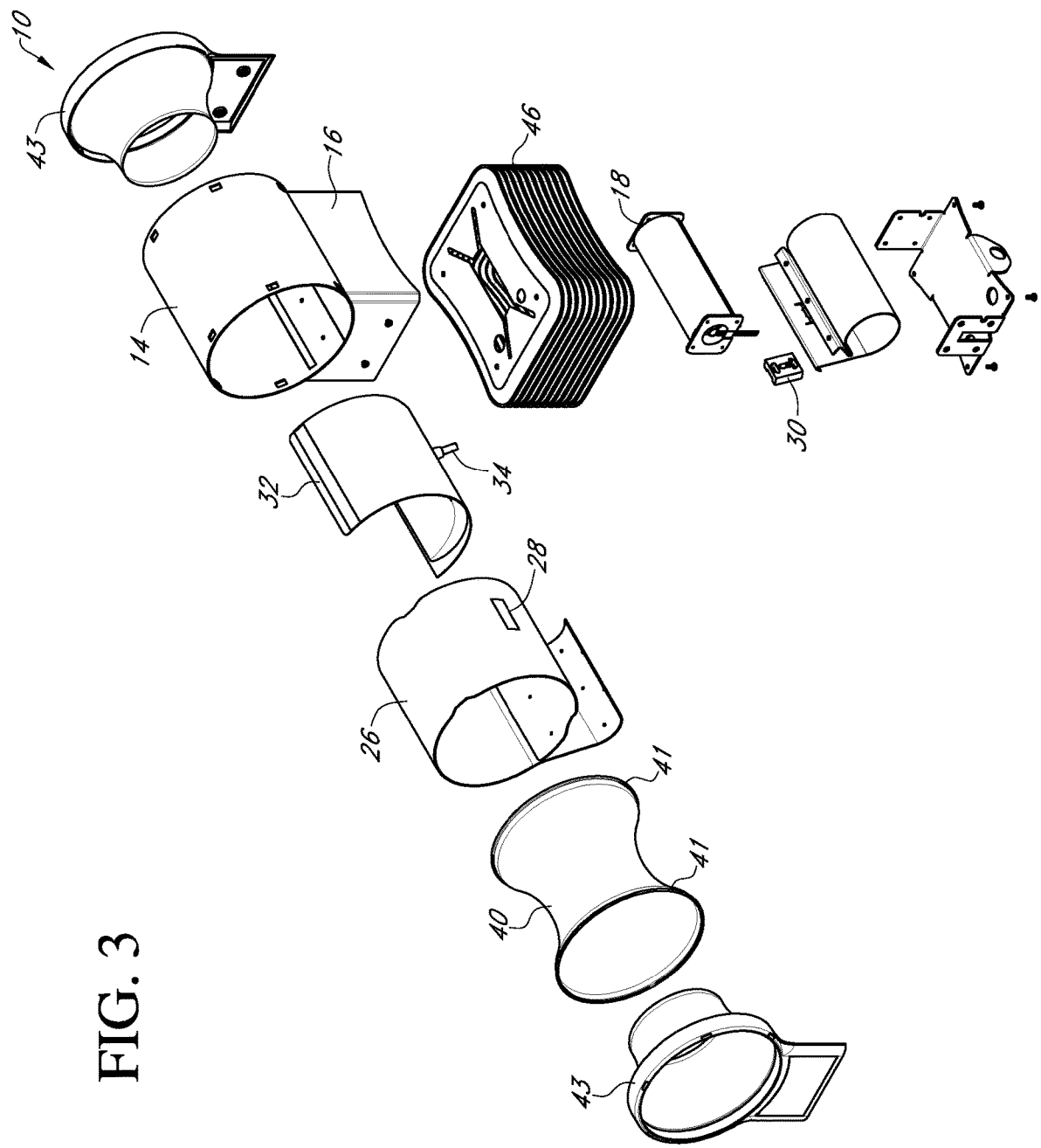
FIG. 3 is a perspective exploded view of a blood pressure device.
Figure 4:
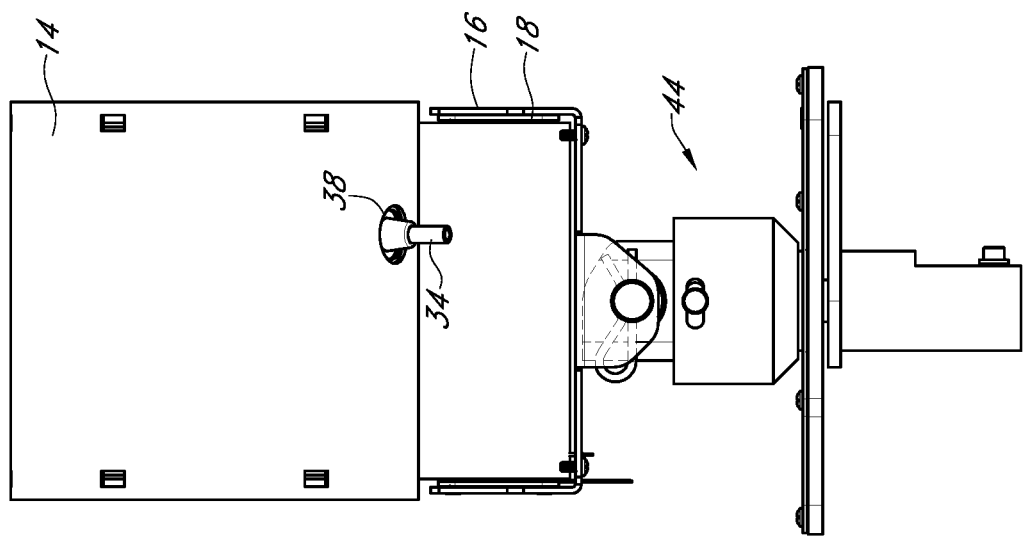
FIG. 4 is a side view of a blood pressure device.
Figure 5:
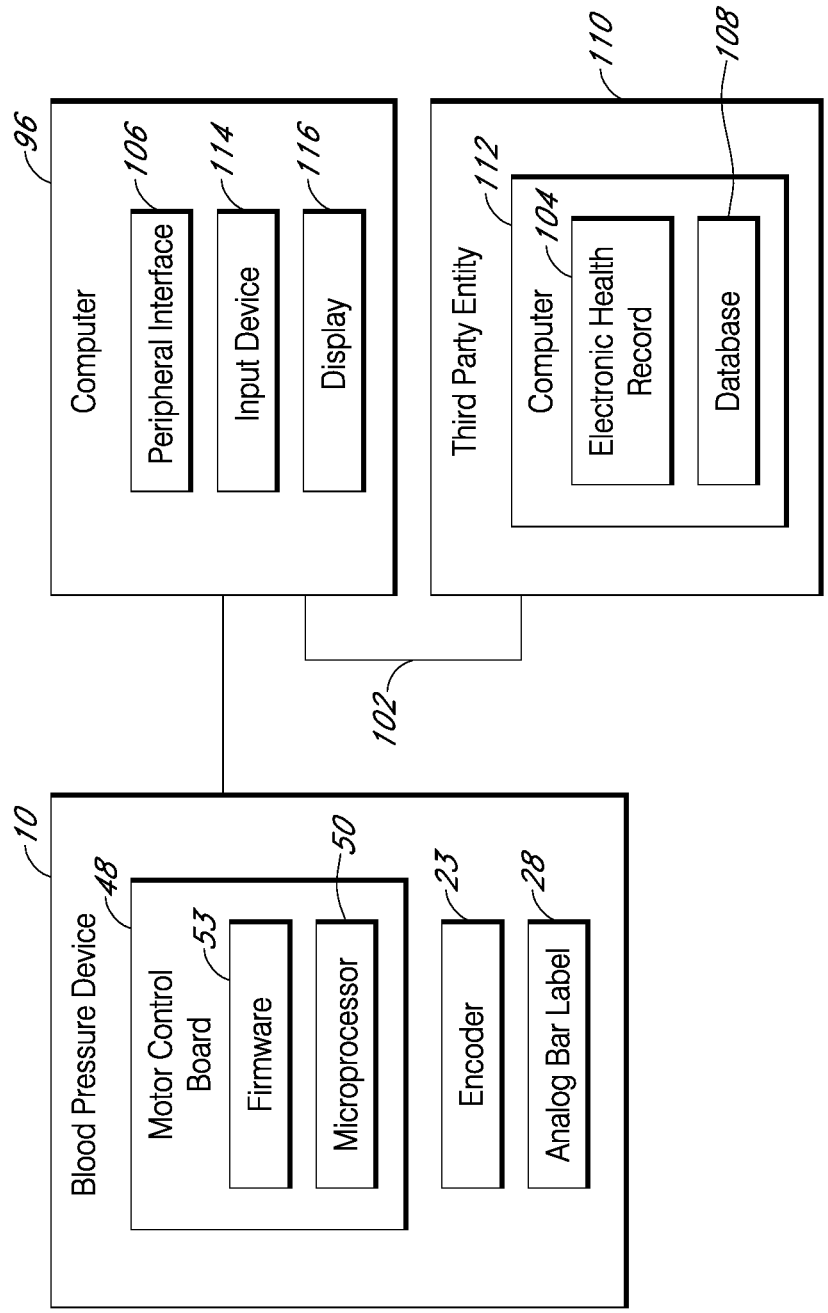
FIG. 5 is a schematic block diagram of an environment for a blood pressure device.

Referring to the Figures, an automated fitted cuff blood pressure and arm circumference measuring device 10 has a cuff and base housing 12. The cuff and base housing 12 has a cylindrical drum 14 that is open at both ends and is attached to a generally rectangular base portion 16. Disposed within the rectangular base portion 16 of the housing 12 is a direct drive reel assembly 18 that includes a reel 20, a motor 22 inside the reel 20 that rotates the reel 20, an encoder 23 mounted to an output shaft of the gear motor 22 or gearhead that measures motor rotation, and in one example a clutch 24 positioned to engage the reel 20 and the motor 22. In another embodiment a motor hub 25 engages the motor 22 and reel 20. The motor 22 provides the torque directly to the reel 20 via the clutch 24 or motor hub 25 and no additional components are required.

A flexible lead band material 26 is connected to and wraps around reel 20. An analog bar label 28 is attached or printed to an outer surface of the band material 26. Also, an infrared sensor 30 and an encoder 23 are associated with the band material 26.

An air bladder 32 having an air nozzle 34 is attached to an inner surface of the band material 26 and is located in the cuff housing 14 but may enter the base housing 16. The nozzle 34 is aligned with and extends through openings 36 and 38 in the band material 26 and the drum 14. Fitted over the bladder 32, and band material 26 inside of drum 14, is a protective skirt 40. To prevent folding and provide an ergonomic feel for the user to interface with the cuff the skirt 40 tapers inwardly from its ends toward the middle and is made of a stretchable material. Embedded within the protective skirt 40 is a piece of rigid plastic 42 to protect a user's arm. In one embodiment the lead material 26 has an extension that prevents pinching. The rigid plastic is positioned to cover the area where the band material 26 and bladder 32 exits the drum 14 to the cuff base 16 and reel 20, to prevent a pinch point. Attached to each end of the drum 14 are cuff housing covers 43 which capture metal hoops 41 that are stitched into each end of the skirt 40. While the metal hoops 41 provide structure to the skirt 40 and an attachment point to the cuff housing covers 43, the cuff housing covers 43 hold the skirt 40 in place and add to the ergonomic feel of the cuff housing 14.

Attached to the base portion 16 of housing assembly 12 is a knuckle support assembly 44 disposed within a bellows cover 46. The knuckle support assembly 44 is configured to allow support for a user's elbow and several degrees of freedom of movement to relax a user's bicep and provide a more accurate reading. The movement of the knuckle assembly permits the arm to be moved into the same position every time a blood pressure measurement is about to be taken with the brachial artery located over the transducer port 47 giving a high level of consistency and accuracy to the blood pressure measurement.

In operation, the device 10 is mounted to a tabletop, kiosk, or the like. An individual inserts their arm through drum 14. The knuckle assembly 44 provides for ergonomic body adjustment that allows for proper alignment of the arm in relation to the body and level of the heart as well as the overall body posture. The tilting of the knuckle support assembly 44 with the spring tension such as a compression spring, gas spring, hydraulic spring, or the like, that are housed inside a protective and flexible bellows 46 compensate for the weight of the device 10, creating a free floating feel when an arm is placed in the device 10. The knuckle assembly 44 also allows for variable user height while still maintaining tricep contact with the lower ID of the cuff. The tilt of the knuckle assembly 44 (Y motion), and the sliding motion of the knuckle assembly 44 (Z motion), allow the natural position of the arm to pull and tilt the device 10 into a natural and comfortable position of the body. This also places the arm closer to heart level and provides the ability of the user to have a postural neutral position which enables a more accurate blood pressure reading. The knuckle assembly 44 also permits rotation creating additional comfort and support. Further, the arm is supported from the elbow to the wrist by a custom designed support board (surfboard) allowing the arm muscles to relax during the blood pressure reading preventing an erroneous measurement. The use of this knuckle assembly 44 allows the accommodation of users of different statures in an otherwise stationary design.

In order to acquire relevant biometric data the computer 96 and corresponding software initiate the motor control board 48 and its firmware 53, which in turn operates the OEM BP module to begin a measurement cycle.

Once positioned, the upper arm circumference can be determined by transmitting information from encoder 23, and/or bar label 28 with sensor 30 to a motor control board 48 having a microprocessor 50 and firmware 53.

The motor control board 48 and firmware 53, based upon signals received from the encoder 23 and/or the analog bar label 28 with sensor 30, determines the position of the lead material band 26 inside the cuff of the housing 12, to provide a positive arm circumference stop. The stop preferably is based upon a 9.5 inch arm in order to prevent the bladder 32 from entering the base 16. A second stop is pre-set to a distance of 18.2 inches to prevent the cuff from unwinding too far through signals received by the motor control board 48 and firmware 53 from the sensor 30 with bar label 28 and/or encoder 23. Additionally, the motor control board 48 and firmware 53 provide additional feedback by measuring current/torque to keep lead material 26 within its operating range and prevent damage to the hardware on the motor control board 48.

Once the arm circumference is determined, the motor control board 48 activates a pump 102 that inflates the bladder 32. The device 10 is designed to operate with and be interchangeable with any OEM BP module design. As the bladder 32 inflates or deflates pressure values are transmitted to the OEM BP module and an individual's blood pressure and pulse rate is determined by the OEM BP module. The motor control board 48 retrieves the BP and heart rate and transmits to the computer 96 for display. In another embodiment the motor control board 48 can be a standalone unit that has the ability to measure blood pressure and collect other biometric feedback based on firmware 53 and hardware on the motor control board 48. Through use of the lead material 26 cinching down on an arm similar to a fitted cuff, the size of the bladder 32 is reduced providing a better signal to noise ratio when taking a blood pressure measurement. The preferred blood pressure measurement uses an oscillometric method. Alternatively, other methods are uses such as an auscultory method where a contact microphone 55 is embedded in the cuff housing 12 or the oscillometric and auscultory methods are use together. The blood pressure device 10 can be coupled with an OEM blood pressor sensor module that is sensitive enough to determine if atrial fibrillation is present, which is reported giving both the heart rate and blood pressure measurement.

Once blood pressure results are determined, the computer 96 can display results and has the option of transmitting the results via an electronic network 102 to an electronic health record (EHR) system 104. For example, the computer 96 has a peripheral interface 106 in direct communication with a database 108 of a third-party entities 110 computer 112 so that the blood pressure result is automatically stored in the user's EHR 104.

Also, the computer 96 has an input device 114 such as a touch screen or the like and a display 116. The software 94 is programmed to provide a user the blood pressure test results and messaging and icons to guide the user through the blood pressure testing process.

What is claimed is:

1. A blood pressure device, comprising:
   a cylindrical drum cuff;
   a direct drive reel assembly having a motor entirely inside of a reel that rotates the reel and an encoder mounted to the motor;
   a flexible lead band material is connected to and wraps around the reel and a sensor is associated with the flexible lead band material; and
   a motor control board determines a positive arm circumference stop and a second pre-set stop based on signals from the encoder,
   wherein the blood pressure device is configured to operate with a blood pressure module to acquire biometric data.

2. The device of claim 1 wherein the device is mounted to one of a group consisting of a table top and a kiosk.

3. The device of claim 1 further comprising a motor control board configured to operate with the blood pressure module.

4. The device of claim 1 wherein the blood pressure module acquires biometric data with a method selected from a group consisting of an oscillometric method, an auscultatory method, and through the presence of arterial fibrillation.

5. A blood pressure device, comprising:
   a cylindrical drum cuff housing;
   a direct drive reel assembly having a motor entirely inside of a reel that rotates the reel and an encoder mounted to the motor;
   a knuckle support assembly attached to the cylindrical drum cuff housing and adapted to provide freedom of movement for postural positioning before and during a blood pressure test; and
   a flexible bellow that houses the knuckle support assembly, wherein the blood pressure device is configured to operate with a blood pressure module to acquire biometric data.

6. The device of claim 5 wherein the knuckle support assembly is adapted to provide ergonomic body adjustment and alignment of an arm in relation to a level of a heart.

7. The device of claim 5 wherein the knuckle support assembly tilts with spring tension.

8. The device of claim 7 wherein the knuckle support assembly rotates to improve a position of the arm.

9. The device of claim 7 wherein the knuckle support assembly slides to position the arm closer to heart level.

10. The device of claim 5 wherein the blood pressure device is configured to support the arm from an elbow to a wrist to permit arm muscles to relax during the blood pressure test.

11. A blood pressure device, comprising:
- a cylindrical drum cuff housing;
- a direct drive reel assembly that includes a motor entirely inside of a reel to rotate the reel and an encoder mounted to the motor;
- a flexible lead band material connected to and wrapped around the reel;
- a sensor associated with the flexible lead band material, wherein the sensor is selected from group consisting of an analog bar label, an infrared sensor, and an encoder; and
- a bladder attached to an inner surface of the flexible lead band material;
- wherein the blood pressure device is configured to operate with a blood pressure module to acquire biometric data.

12. The device of claim 11 further comprising a protective skirt fitted over the bladder and the flexible lead band material.

13. The device of claim 12 wherein the protective skirt tapers inwardly from its ends toward its middle.

14. The device of claim 12 wherein a piece of rigid plastic is embedded within the protective skirt.

15. The device of claim 12 wherein each end of the protective skirt has cuff housing covers that capture metal hoops attached to the protective skirt.

16. The device of claim 11 wherein the flexible lead material is adapted to cinch down on an arm and reduce the bladder's volume.

* * * * *